United States Patent [19]

Hennart et al.

[11] 4,205,066

[45] May 27, 1980

[54] BAIT COMPOSITIONS FOR ANTHROPOPHILIC FLIES

[75] Inventors: Claude Hennart, Seraincourt; Bernard Rabussier, Avanton; Jean-Pierre Mandon, Chasseneuil-du-Poitou; Joel Sapin, Ligugé, all of France

[73] Assignee: Airwick Industries, Inc., Carlstadt, N.J.

[21] Appl. No.: 949,600

[22] Filed: Oct. 10, 1978

[30] Foreign Application Priority Data

Oct. 10, 1977 [LU] Luxembourg .......................... 78277

[51] Int. Cl.² ............................................ A01N 7/14
[52] U.S. Cl. ...................................................... 424/84
[58] Field of Search ........................................... 424/84

[56] References Cited

U.S. PATENT DOCUMENTS

| | | | |
|---|---|---|---|
| 1,059,888 | 4/1913 | Maire | 424/84 |
| 3,846,557 | 11/1974 | Mulla et al. | 424/84 |
| 4,122,165 | 10/1978 | Kinger et al. | 424/84 |

FOREIGN PATENT DOCUMENTS

| | | | |
|---|---|---|---|
| 1403637 | 8/1975 | United Kingdom | 424/84 |
| 1428393 | 3/1976 | United Kingdom | 424/84 |

*Primary Examiner*—Donald B. Moyer
*Attorney, Agent, or Firm*—Harry Falber

[57] ABSTRACT

A composition which can be used as a bait for anthropophilic flies, containing a synergistic mixture of at least one alkene having 19 to 24 carbon atoms, in which the ethylenic bond is located after a carbon atom in the range between the 7-position and the 11-position, and at least one aminoacid source selected from the group comprising the biochemical class of protides.

13 Claims, No Drawings

BAIT COMPOSITIONS FOR ANTHROPOPHILIC FLIES

The present invention relates to lure compositions which can be used as baits, are intended for combating anthropophilic flies and are distinguished by their very high luring power with regard to the said flies.

Anthropophilic flies are insects which are annoying and/or harmful to man, in particular because of the pathogenic germs which they carry (trypanosomes, rickettsiae, tuberculosis bacillus, leprosy bacillus, chlorera vibrio, typhoid bacillus, dysentery bacillus, anthrax-type bacteria, diphtheria bacillus, amoebae, diverse protozoa and eruptive fever virus) and the larvae of which can, furthermore, cause intestinal or cutaneous myiases.

It is understandable why man seeks to destroy the insects of this category everywhere in the world. These are, above all, the Diptera of the families Muscidae, Sarcophagidae and Tachinidae.

Baits, in combination with traps or insecticides, in general do not have any disadvantages but, on the other hand, their effectiveness is tied to their degree of luring which they exert on the insects, since it is necessary that the latter come to feed for the bait to act.

Diverse substances have been specified for playing the role of lure in insecticidal compositions which can be used as baits. These are, in particular, malt (French Pat. No. 1,141,605), orange peel oil (French Pat. No. 1,605,359), vanillin (French Pat. No. 2,303,477 and German Pat. No. 2,510,450), terpineol, farnesol, geraniol or phenylethanol (French Pat. No. 2,303,477), hydrolysis products from living cells (French Pat. No. 2,325,327), formaldehyde (British Pat. No. 597,822), combinations of tertiary amines and carboxylic acids (U.S. Pat. No. 3,996,349), aliphatic lactones (Japanese Application No. 76/79,727), chlorinated alkenes (Japanese Application No. 76/70,825), extracts from aucuba fruit (Japanese Application No. 72/37,011) and aliphatic monoesters of polyols (Japanese Application No. 73/58,126).

Recently, lure compositions which are stronger than those quoted above have been described in French Application No. 2,707,649. These compositions comprise a food, namely sucrose, an insecticidal agent selected from the group comprising trichlorphon, arprocarb, dichlorvos, fenchlorphos and O,O-dimethyl O-1,3-bis-(methoxycarbonyl)isopropenyl phosphate and a lure, namely cis-tricosene-9.

Novel bait compositions have now been found, which exert a very strong lure effect on anthropophilic flies. These compositions comprise a food which can be consumed by the insects and which is different from sugar and is used alone or in addition to sugar, as well as a lure agent, this combination having a luring action on the flies which at the same time is much higher than that obtained with the same baits in which the food consists solely of sugar, and significantly higher than that which would result from a simple addition of the efficacies of the food and the lure agent in a mixture thereof. Such a different food is a nutrient material which is composed of or contains a source of aminoacid or aminoacids.

In fact, there is a synergism between these alkenes and the aminoacid sources such that the luring action of the baits is greater when they contain, at the same time, such an alkene and an aminoacid source than when they contain only one of these two constituents, even at a higher level.

Baits of this type can be used in the dry state or in the moist state.

The invention thus relates to a composition which can be used as a bait for anthropophilic flies, containing a lure and a food, wherein the lure is selected from the group comprising stereoisomers of cis-, trans- and cis/-trans-configuration of straight-chain or branched alkenes having 19 to 24 carbon atoms, in which the ethylenic bond is located after a carbon atom in the range between the 7-position and the 11-position, or from mixtures of two or more of these alkenes, and wherein the food is or contains an aminoacid source.

Preferably, this bait is combined with an insecticidal agent which causes the destruction of the insects consuming the latter.

The preparation of the compositions according to the invention is in general effected by simply mixing the constituents; however, when the compositions contain an insecticidal agent, it is preferable, in certain cases, for a better distribution of the active insecticidal material and the colorant, to proceed as follows:
(a) mixing the nutrient constituents,
(b) dissolving the active insecticidal material and the colorant in a sufficiently volatile solvent, such as acetone or methylene chloride,
(c) spraying the solution b over the mixture a and
(d) completely evaporating the volatile solvent.

The optimum particle size of the composition varies depending on the type of insects which it is desired to destroy; in general, the particle size should be the finer, the smaller the insect for which the bait is intended. Preferably, the particle size is between 0.05 mm and 1 mm.

The bait can be in the free form or alternatively in a form, such as granules or tablets, agglomerated with or without the aid of a binder.

Moreover, the bait can be in the dry or moist form, but in general it is in the dry form and contains only the equilibrium humidity which results from the bait being humidified by the surrounding air.

The bait can also be fixed on an inert support or absorbed therein, and this inert support can consist, for example, of paper, blotting paper, cardboard, a plastic material, such as polystyrene, polyvinyl chloride, polyvinyl acetate and cellulose acetate, glass, pumice, crushed marble or silica or silicate minerals.

Moreover, the lure can consist of a single or of several alkenes and, in the latter case, cis-tricosene-9-can advantageously be one of the alkenes.

Examples which may be mentioned of the alkenes defined above are the following, in the cis-, trans and cis/trans-configuration: 2-methyl-octadecene-9, nonadecene-9, 2-methyl-nonadecene-9, eicosene-9, 2-methyl-eicosene-8, 8-methyl-eicosene-8, 10-methyl-eicosene-8, 2-methyl-eicosene-9, 10-methyl-eicosene-9, 19-methyl-eicosene-9, heneicosene-9, 2-methyl-heneicosene-8, 8-methyl-heneicosene-8, 2-methyl-heneicosene-9, 10-methyl-heneicosene-9, 19-methyl-heneicosene-9, 20-methyl-heneicosene-9, 19-ethyl-heneicosene-9, docosene-8, docosene-9, 2-methyl-docosene-8, 8-methyl-docosene-8, 10-methyl-docosene-8, 2-methyl-docosene-9, 10-methyl-docosene-9, 19-methyl-docosene-9, 20-methyl-docosene-9, 21-methyl-docosene-9, 19-ethyl-docosene-9, 20-ethyl-docosene-9, tricosene-7, tricosene-8, tricosene-9, tricosene-10, tricosene-11, 2-methyl-tricosene-8, 8-methyl-tricosene-8, 2-methyl-tricosene-9, 9-methyl-tricosene-9, 10-methyl-tricosene-9, 19-methyl-tricosene-9, 20-methyl-tricosene-9, 21-methyl-tricosene- 9, 22-methyl-tricosene-9, tetracosene-9 and tetracosene-10.

The lure is present in the composition in a proportion of 0.05 to 2 percent, relative to the weight of the composition, and preferably in a proportion of 0.1 to 1 percent.

More preferably, this proportion is between 0.1 and 0.5 percent.

Amongst the alkenes defined above, those in which the ethylenic bond is located after the carbon atom in the 8-position and, above all, the 9-position, are of very particular interest in the compositions according to the invention.

Amongst the latter compounds, those which have a straight chain and, in particular, the cis-stereoisomers of these n-alkenes, for example cis-nonadecene-9, cis-docosene-9, cis-heneicosene-9 and cis-tricosene-9, exert a very strong luring action on anthropophilic flies when they are combined with an aminoacid source.

Furthermore, it is also particularly surprising that, in combination with an aminoacid source according to the invention, the cis-, trans- and cis/trans-alkenes other than cis-tricosene-9, which hitherto had been stated to be clearly less effective than cis-tricosene-9, exert a luring action of the same order of magnitude as that of cis-tricosene-9 in the novel compositions according to the invention.

Amongst the alkenes quoted above, cis-tricosene-9 is of particular interest.

The aminoacid source is selected from the group comprising the biochemical class of protides, i.e. from the actual aminoacids, the peptides and the proteins.

Amongst the aminoacids, the following may be mentioned, for example: alanine, arginine, aspartic acid, cysteine, cystine, glutamic acid, glycine, histidine, hydroxyproline, isoleucine, leucine, lysine, methionine, phenylalanine, proline, serine, threonine, tryptophan, tyrosine and valine.

The peptides which can be used are natural or synthetic compounds which are formed by joining a relatively restricted number of aminoacids. Amongst these, the following may be mentioned, for example: glutathione which is present in yeast and in intracellular components of mammalian tissues, carnosine which is present in the striated muscles of mammals and fish, anserine which is present in the striated muscles of birds, polyglutamic acid which is present in microorganisms, and the diverse polypeptide chains which are produced by incomplete hydrolysis of proteins.

The proteins are present in all the tissues of living animals and plants. They are formed by joining a large number of aminoacids. Amongst the proteins, the following may be mentioned, for example: zein, gliadin, hordein, arachin and the globulins, which are present in vegetable seeds, myosin, actin and tropomyosin, which are present in animal muscle fibres, serum albumin, lipoproteins, haemoglobin and fibrinogen, which are present in blood, ovalbumin, conalbumin, lysozyme and avidin, which are present in eggs, casein and lactoglobulin, which are present in milk, collagen and elastin, which are present in sinews and connective tissues, reticulin which is present in skin and fatty tissues, and cornein, ichthyocol and elastoidin, which are present in fish tissues.

The proportion of aminoacid source in the food is between 2 and 100% by weight of the food, the remainder, if any, consisting of a nutrient material which is not of the protide type.

Preferably, the proportion of aminoacid source in the food is at least equal to 10%.

The aminoacid source is used in the isolated state or in the crude state in the previously dehydrated material which constitutes its medium of origin.

The products of complete or partial hydrolysis of vegetable or animal proteins in the crude state may be mentioned as examples of aminoacids and peptides in the crude state.

The compositions according to the invention, in which at least a part of the aminoacid source consists of a hydrolysis product of vegetable and/or, if desired, animal proteins, exert a particularly high luring effect on anthropophilic flies.

The following may be mentioned as examples of materials containing proteins in the crude state and, if appropriate, peptides, the values in brackets representing the average percentage of protides present:

A. Dry fruit. Dry apricots (5.2), dried dates (2.2), dried figs (3.1), dried peaches (3.0), dried pears (2.3), dried apples (3.0), dried plums (2.3), dry grapes (2.3), almonds (18.6), peanuts (30.6), hazelnuts (12.7), walnuts (15.0) and cacao (20.4).

B. Dry vegetables. Dried cabbage (13.7), dried carrot (4.0), dried haricot bean (22.0), dried lentil (25.7), dried onion (10.1), dry pea (24.5) and dried potato (7.1).

C. Cereals. Porridge oats (13.0), wheat flour (12.2), maize flour (9.2), rice flour (7.4), rye flour (11.0), soya flour (35.9), wheat germ (25.2), pearl barley (9.0) and dried wheat bread (9.8).

D. Dairy products. Whole milk powder (25.8), skimmed milk powder (35.6), Emmental cheese (28.6), Limbourg cheese (23.5), Parmesan cheese (36.3), Roquefort cheese (21.7) and egg powder (48.2).

E. Meat. Cattle meal (65), cattle offal meal (72), horse meal (76), rabbit meal (74), mutton meal (68), pork meal (69), whale meal (78), poultry meal (73) and poultry offal (75).

F. Fish and shellfish. Cod meal (63), tunny meal (82), shrimp meal (67) and herring meal (70).

G. Miscellaneous. Dry gelatine (85.6), dark chocolate (5.5), milk chocolate (6.0), molasses (2.4), pressed brewers' yeast (13.3), dry brewers' yeast (46.1) and dry mushrooms (40).

The non-protidic nutrient material, if present, is selected from the group comprising the carbohydrates, for example sucrose, maltose, lactose, glucose, fructose, galactose, raffinose, invert sugar and honey and starch, and the lipids.

The said carbohydrates and lipids can be present naturally in the material containing the aminoacid source in the crude state, in addition to diverse natural components, such as celluloses, or they can alternatively be added to the said materials in the composition.

Foods of vegetable origin, which are low in protides, such as tapioca, may be indicated as examples of carbohydrates which can be added to the composition, in addition to those quoted above.

Butter, vegetable oils, lard, tallow and fish oils may be indicated as examples of lipids which can be added to the composition.

The insecticidal agent, if present in the compositions according to the invention, can be selected from all those which act on the insects by ingestion: the preferred insecticidal agents are selected from the group comprising the aromatic or hetero-aromatic esters of N-substituted carbamic acids and the organo-phosphorus compounds.

Examples which may be mentioned of suitable carbamic acid esters are: 3-methyl-pyrazol-5-yl dimethylcarbamate, 1-dimethylcarbamyl-5-methyl-pyrazol-3-yl dimethylcarbamate (dimetilan), 2-isopropoxy-phenyl methylcarbamate (arprocarb), 1-phenyl-3-methyl-pyrazol-5-yl dimethylcarbamate (Pyrolan), 2-propyl-4-methyl-pyrimid-6-yl dimethylcarbamate (Pyramat), 2-(1,3-dioxolan-2-yl)phenyl methylcarbamate (dioxacarb), 5,6,7,8-tetrahydronaphth-2-yl N-methylcarbamate, 2-methyl-quinol-8-yl N-methylcarbamate, ortho-tert.-butylphenyl N-methylcarbamate, ortho-tert.-butoxyphenyl N-methylcarbamate, ortho-(prop-2-ynyloxy)-phenyl N-methylcarbamate, ortho-sec.-butylphenyl N-methylcarbamate, ortho-sec.-butoxyphenyl N-methylcarbamate, 2,6-di-tert.-butylphenyl N-methylcarbamate, 2,6-di-sec.-butylphenyl N-methylcarbamate, 2,6-diisopropylphenyl N-methylcarbamate, 2-tert.-butyl-6-methylphenyl N-methylcarbamate, 5,5-dimethylcyclohex-1-en-3-onyl dimethylcarbamate (dimetan) and 2,3-isopropylidenedioxyphenyl N-methylcarbamate (bendiocarb).

Amongst the carbamic acid esters, dimetilan, dioxacarb and 2-methyl-quinol-8-yl N-methylcarbamate are very particularly preferred.

Examples which may be mentioned of suitable organo-phosphorus compounds are: O,O-dimethyl O-(2,2-dichlorovinyl) phosphate (dichlorvos), O,O-dimethyl (1,2-dibromo-2,2-dichloroethyl) phosphate (Dibrom), O,O-dimethyl S-(4-aza-6-chloro-2-oxo-benzoxazol-3-yl)methyl thiophosphate (azamethiphos), ethyl 2-(dimethoxythioxo-phosphoranylthio)-succinate (malathion), O,O-diethyl O-(2-isopropyl-6-methyl-pyrimid-4-yl) thiophosphate (diazinon), O,O-dimethyl O-(4-bromo-2,5-dichlorophenyl) thiophosphate (bromophosethyl), O,O-dimethyl O-(3-methyl-4-nitrophenyl) thiophosphate (fenitrothion), O,O-dimethyl O-(2-methoxycarbonylprop-1-enyl) thiophosphate (methacriphos), O,O-diethyl O-(3,5,6-trichloropyrid-2-yl) thiophosphate, O,O-dimethyl O-(2,4,5-trichlorophenyl) thiophosphate (fenchlorphos), O,O-dimethyl O-(2,5-dichloro-4-iodophenyl) thiophosphate (iodofenphos), O,O-diethyl O-(3,5,6-trichloro-pyrid-2-yl)-ethyl thiophosphate (chlorpyriphos), O,O-dimethyl O-(3,5,6-trichloro-pyrid-2-yl)-methyl thiophosphate (chlorpyriphos-methyl), O-(2-isopropoxycarbonyl-1-methylvinyl) O-methyl N-ethylphosphoramidothioate (propetamphos), S-(2-aza-2-oxo-bezoxazol-3-yl)-methyl O,O-diethyl dithiophosphate and dimethyl 2,2,2-trichloro-1-hydroxyethyl-phosphonate (trichlorphon).

Amongst these organo-phosphorus compounds, those of which the vapour pressure is less than 0.013 millibar at 20° C., and in particular malathion, azamethiphos, fenitrothion and binary and ternary mixtures thereof, are very particularly preferred.

In addition to the carbamic acid esters and organo-phosphorus compounds, or in combination with these substances, it is possible to use other insecticidal materials, such as natural pyrethrins, rotenone, synthetic pyrethrinoids, N,N'-dibutyl-parachlorobenzene-sulphonamide, 1,2,4,5,6,7,8,8,-octachloro-3a,4,7,7a-tetrahydro-4:7-methano-indane, the gamma stereoisomer of 1,2,3,4,5,6-hexachlorocyclohexane, endo-oxo-1,2,3,4,10,10-hexachloro-6,7-epoxy-1,4,4a,5,6,7,8,8a-octahydro-1:4,5:8-dimethanonaphthalene, sodium fluoride and boric acid and its salts.

The concentration of insecticidal agent in the bait can vary. Advantageously, it is between 0.01 and 8% by weight, and preferably between 0.2 and 5%.

Amongst the compositions according to the invention, those are of particular interest which contain about 10 to 75% by weight of aminoacid source, about 0.1 to 8% by weight of insecticide and about 0.05 to 1% by weight of lure, the remainder of the composition consisting essentially of a water-soluble carbohydrate and all the percentages by weight being relative to the total weight of the composition.

Preferably, the aminoacid source contains, at the same time, proteins and products resulting from a more or less extensive hydrolysis of proteins, such as mixtures of meat meals and hydrolysis products of vegetable and/or animal proteins. Such compositions according to the invention contain, for example: about 2.5 to 15% by weight of a product of a complete and/or partial hydrolysis of vegetable and/or animal proteins, but preferably vegetable proteins, about 0.1 to 8% by weight of an insecticide, for example dimetilan or azamethiophos, and about 0.05 to 2% by weight of at least one alkene as defined above, the remainder of the composition consisting essentially of a water-soluble carbohydrate.

In particular, the following compositions according to the invention are especially attractive for the insects: about 45 to 72.5% by weight of meat meal, about 2.5 to 15% by weight of a hydrolysis product of proteins, about 0.1 to 6% by weight of an insecticide and about 0.5 to 1% by weight of an alkene as defined above, the remainder of the composition consisting essentially of a water-soluble carbohydrate, and all these proportions being relative to the total weight of the composition.

Further secondary materials, which may or may not be nutrients, can be added to the compositions according to the invention with a view to enhancing the lure effect on a particular species of harmful insects. Amongst these secondary materials which may be mentioned are natural or artificial flavours of cheese, meat and fruit, pollen extracts, thymol, scatole, indole, eugenol, paraformaldehyde, hexamethylene-tetramine, ammonium carbamate, aliphatic amines, papain, pancreatin, aliphatic acids, vanillin, 3-chloro-3-methylbutene-1 and 1-chloro-3-methylbutene-2.

If desired, the composition can also include an inert support and/or a binder, such as a natural or synthetic glue, and/or a colorant or pigment and/or a stabiliser.

The importance of the compositions according to the invention is demonstrated by the experiments below:

EXPERIMENT A

The following baits A-0 and A-1 were prepared as a fine powder (values in percent by weight), wherein the insecticide serves as "tracer" since it permits a precise determination of the luring action of the bait by counting the numbers of insects which have fed on it.

TABLE 1

| Compositions | A-0 | A-1 |
|---|---|---|
| Cattle meal | 63.70 | 63.70 |
| Sucrose | 20.00 | 20.00 |
| Dimetilan[a] | 5.00 | 5.00 |
| Hydrolysis product of vegetable proteins | 10.00 | 9.88 |
| cis-Tricosene-9 | — | 0.12 |
| Organol Red BS | 0.80 | 0.80 |
| Potassium sorbate | 0.50 | 0.50 |

[a] 1-Dimethylcarbamyl-5-methyl-pyrazol-3-yl N,N-dimethylcarbamate.

These baits were glued onto a cylindrical polystyrene support of 35 mm diameter by 200 mm height, the latter being moistened with methylene chloride to make it adhesive. After drying, these cylinders were placed upright and coaxially in a perforated enclosure of cylindrical shape, which was made from black-coloured polystyrene of 90 mm diameter by 200 mm height and the perforations of which were vertical slits of 13 by 155 mm.

The devices thus prepared were installed, two meters from one another, in a room of 40 m³, kept at a temperature of 25° C. and at a relative humidity of 45±5 and illuminated uniformly by 1,250 lux at the level of the devices.

Flies of the species Musca domestica were released every 15 minutes into the room and the proportion of dead flies in the immediate vicinity of each bait was noted. The operation was repeated 18 times, permutating the position of the devices each time.

The overall results of the group of experiments are summarised in the table below (percentages of dead flies at each reading).

TABLE II

| Time elapsed in minutes | A-0 | A-1 |
|---|---|---|
| 15 | 26.0 | 46.0 |
| 30 | 29.6 | 57.3 |
| 45 | 31.2 | 61.6 |
| 60 | 32.4 | 63.8 |
| 90 | 32.9 | 65.7 |
| 120 | 33.3 | 66.5 |

EXPERIMENT B

The devices used contained the baits A-0 and A-1, as described in Experiment A. Twentysix devices were placed, in pairs of the same room, in the houses of thirteen people living in the country in France, in the Vienne département. A permutation was carried out every three days and, after eight permutations, the quantities of dead flies noted on each permutation in each device or in the immediate vicinity were added up, and the results were entered in the following table:

TABLE III

| Test Points | A-0 | A-1 | Relative effectiveness |
|---|---|---|---|
| I | 104 | 1,352 | 13.0 |
| II | 320 | 1,880 | 5.9 |
| III | 8 | 144 | 18.0 |
| IV | 61 | 815 | 13.4 |
| V | 72 | 272 | 3.8 |
| VI | 93 | 1,319 | 14.2 |
| VII | 12 | 448 | 37.3 |
| VIII | 62 | 1,140 | 17.3 |
| IX | 12 | 235 | 19.6 |
| X | 47 | 628 | 13.4 |
| XI | 54 | 553 | 10.2 |
| XII | 179 | 546 | 3.1 |
| XIII | 74 | 566 | 7.6 |
| TOTALS | 1,102 | 9,898 | 9.0 |

The results of the Experiments A and B show that the baits according to the invention, containing cis-tricosene-9 and an aminoacid source, are more effective than those which do not contain cis-tricosene-9.

EXPERIMENT C

The following baits C-0 and C-1 were prepared as a fine powder (values in percent by weight):

TABLE IV

| Composition | C-0 | C-1 |
|---|---|---|
| Cattle meal | — | 10.0 |
| Sucrose | 97.9 | 87.9 |
| Dimetilan (a) | 2.0 | 2.0 |
| cis-Tricosene-9 | 0.1 | 0.1 |

These baits were distributed in Petri dishes and the test was carried out by effecting permutations between the positions occupied by the baits and by releasing flies, as stated in Experiment A.

On each permutation, after three hours, the number of dead flies in each Petri dish or in the immediate vicinity was counted and at the end of the tests the relative effectiveness between C-1 and C-0 was calculated by dividing the total of dead flies in C-1 by that of dead flies in C-0.

The relative effectiveness thus found was 3.7.

Following the same procedure, but replacing the cattle meal in C-1 by the same quantity of another aminoacid source, the following relative effectivenesses were found:

Hydrolysis product of cattle meat: 1.9
Hydrolysis product of poultry meat: 1.7
Hydrolysis product of vegetable proteins: 1.8
Anhydrous ovalbumin: 1.8
Dehydrated gelatine: 2.2
Racemic alpha-alanine: 1.6
Laevo-rotatory leucine: 2.9
Laevo-rotatory cystine: 3.2
Racemic valine: 2.4

The results of this experiment show that the baits containing cis-tricosene-9 and an aminoacid source are more effective than those not containing this same source.

EXPERIMENT D

The following baits D-1, D-2 and D-3 were prepared as a fine powder (values in percent by weight):

TABLE V

| Composition | D-1 | D-2 | D-3 |
|---|---|---|---|
| Aminoacid source[b] | — | 10.0 | 5.0 |
| Sucrose | 40.0 | 40.0 | 40.0 |
| Glass Powder | 59.3 | 49.5 | 54.4 |
| Dimetilan[a] | 0.5 | 0.5 | 0.5 |
| cis-Tricosene-9 | 0.2 | — | 0.1 |

[b]Mixture consisting of chicken meat proteins and hydrolysis product of vegetable proteins, the latter containing short-chain peptides and most of the amino-acids present in vegetable protein materials.

These baits were each glued onto a 9×9 cm polystyrene panel by means of a layer of glue consisting of an emulsion of polyvinyl acetate. The weight of each bait thus glued was approximately two grams. Each panel was placed on the bottom of a polystyrene box having a square base (10×10 cm), a height of 5 cm and a completely open upper face.

The devices thus prepared were placed in a triangle, two meters from one another, in a room of 40 m³ kept at a temperature of 25°/26° C. and at a relative humidity of 40.

200 flies of the species Musca domestica were released into the room, and the proportion of dead flies in the immediate vicinity of each device and in each of the latter was noted every fifteen minutes. The operation was repeated 6 times, permutating the position of the devices each time.

The overall results of the group of tests are summarised in the table below (average number of dead flies per test); one column indicates the expected results for the bait D-3, i.e. those which could normally be expected from its composition and from the results noted for the baits D-1 and D-2.

TABLE VI

| | Time elapsed in minutes | D-1 | D-2 | D-3 Expected result | D-3 Observed result | Relative synergism |
|---|---|---|---|---|---|---|
| Total number of dead flies | 15 | 0.2 | 2.2 | 1.2 | 9.4 | 7.84 |
| | 30 | 1.0 | 3.2 | 2.1 | 14.0 | 6.66 |
| | 45 | 1.2 | 4.2 | 2.7 | 17.8 | 6.60 |
| | 60 | 2.0 | 5.0 | 3.5 | 21.8 | 6.24 |
| | 90 | 2.9 | 5.9 | 4.4 | 28.1 | 6.40 |
| | 120 | 4.6 | 6.2 | 5.4 | 33.2 | 6.15 |
| | 150 | 5.5 | 7.0 | 6.25 | 35.9 | 5.96 |
| | 180 | 7.8 | 8.8 | 8.3 | 39.4 | 4.75 |
| Number of dead flies inside each device at the end of the test | | 2.5 | 3.9 | 3.2 | 30.8 | 9.66 |

EXPERIMENT E

The following baits E-1, E-2 and E-3 were prepared as a fine powder (values in percent by weight):

TABLE VII

| Compositions | E-1 | E-2 | E-3 |
|---|---|---|---|
| Aminoacid Source[b] | — | 10.0 | 5.0 |
| Sucrose | 40.0 | 40.0 | 40.0 |
| Glass powder | 58.5 | 49.5 | 54.0 |
| Dimetilan[a] | 0.5 | 0.5 | 0.5 |
| cis-Heneicosene-9 | 1.0 | — | 0.5 |

[a] 1-Dimethylcarbamyl-5-methyl-pyrazol-3-yl dimethylcarbamate
[b] Mixture consisting of chicken meat proteins and hydrolysis product of vegetable proteins, the latter containing short-chain peptides and most of the aminoacids present in vegetable protein materials.

These baits were each glued onto a 9×9 cm polystyrene panel by means of a layer of glue consisting of an emulsion of polyvinyl acetate. The weight of each bait thus glued was approximately two grams. Each panel was placed on the bottom of a polystyrene box having a square base (10×10 cm), a height of 5 cm and a completely open upper face.

The devices thus prepared were placed in a triangle, two meters from one another, in a room of 40 m³ kept at a temperature of 25°/26° C. and at a relative humidity of 40.

Flies of the species Musca domestica were released into the room, and the proportion of dead flies in the immediate vicinity of each device and in each of the latter was noted every fifteen minutes. The operation was repeated 3 times, permutating the position of the devices each time.

The overall results of the group of tests are summarised in the table below (average number of dead flies per test); one column indicates the expected results for the bait E-3, i.e. those which could normally be expected from its composition and from the results noted for the baits E-1 and E-2.

TABLE VIII

| Time elapsed in minutes | E-1 | E-2 | E-3 Expected result | E-3 Observed result | Relative synergism |
|---|---|---|---|---|---|
| Total number of dead flies 15 | 10.3 | 15.7 | 13.0 | 23.0 | 1.77 |
| 30 | 10.9 | 19.3 | 15.1 | 30.0 | 1.99 |
| 60 | 11.8 | 21.7 | 16.75 | 32.0 | 1.91 |
| Number of dead flies inside each device at the end of the test | 7.7 | 16.2 | 12.0 | 25.5 | 2.12 |

EXPERIMENT F

This was carried out as Experiment E, using the following baits F-1, F-2 and F-3:

TABLE IX

| Composition | F-1 | F-2 | F-3 |
|---|---|---|---|
| Aminoacid source (b) | — | 10.0 | 5.0 |
| Sucrose | 40.0 | 40.0 | 40.0 |
| Glass powder | 59.1 | 49.5 | 54.3 |
| Dimetilan (a) | 0.5 | 0.5 | 0.5 |
| cis-Docosene-9 | 0.4 | — | 0.2 |

The overall results of the group of tests are summarised in the following table:

TABLE X

| Time elapsed in minutes | F-1 | F-2 | F-3 Expected result | F-3 Observed result | Relative synergism |
|---|---|---|---|---|---|
| Total number of dead flies 15 | 4.3 | 11.1 | 7.7 | 41.2 | 5.35 |
| 30 | 5.2 | 12.1 | 8.65 | 46.9 | 5.42 |
| 60 | 7.1 | 13.5 | 10.3 | 52.6 | 5.11 |
| Number of dead flies inside each device at the end of the test | 5.7 | 9.0 | 7.35 | 38.8 | 5.28 |

EXPERIMENT G

This was carried out as Experiment E, using the following baits G-1, G-2 and G-3:

TABLE XI

| Composition | G-1 | G-2 | G-3 |
|---|---|---|---|
| Aminoacid source (b) | — | 10.0 | 5.0 |
| Sucrose | 40.0 | 40.0 | 40.0 |
| Glass powder | 58.9 | 49.5 | 54.2 |
| Dimetilan (a) | 0.5 | 0.5 | 0.5 |
| cis-Heneicosene-9 | 0.2 | — | 0.1 |
| cis-Docosene-9 | 0.4 | — | 0.2 |

The overall results of the group of tests are summarised in the following table:

TABLE XII

| Time elapsed in minutes | G-1 | G-2 | G-3 Expected result | G-3 Observed result | Relative synergism |
|---|---|---|---|---|---|
| Total number of dead flies  15 | 7.3 | 10.7 | 9.0 | 38.3 | 4.26 |
| 30 | 9.5 | 12.0 | 10.75 | 42.4 | 3.94 |
| 60 | 11.5 | 15.0 | 13.25 | 45.3 | 3.42 |
| Number of dead flies inside each device at the end of the test | 8.1 | 12.7 | 10.4 | 40.9 | 3.93 |

EXPERIMENT H

This was carried out as Experiment E, using the following baits H-1, H-2 and H-3:

TABLE XIII

| Composition | H-1 | H-2 | H-3 |
|---|---|---|---|
| Aminoacid source[b] | — | 10.0 | 5.0 |
| Sucrose | 40.0 | 40.0 | 40.0 |
| Glass powder | 59.2 | 49.5 | 54.35 |
| Dimetilan[a] | 0.5 | 0.5 | 0.5 |
| cis-Heneicosene-9 | 0.1 | — | 0.05 |
| cis-Tricosene-9 | 0.2 | — | 0.1 |

The overall results of the group of tests are summarised in the following table:

TABLE XIV

| Time elapsed in minutes | H-1 | H-2 | H-3 Expected result | H-3 Observed result | Relative synergism |
|---|---|---|---|---|---|
| Total number of dead flies  15 | 5.5 | 16.6 | 11.05 | 36.7 | 3.32 |
| 30 | 8.0 | 18.8 | 13.4 | 40.6 | 3.03 |
| 60 | 8.8 | 21.2 | 15.0 | 42.9 | 2.86 |
| Number of dead flies inside each device at the end of the test | 6.4 | 18.5 | 12.45 | 41.5 | 3.33 |

EXPERIMENT I

This was carried out as Experiment E, using the following baits I-1, I-2 and I-3:

TABLE XV

| Composition | I-1 | I-2 | I-3 |
|---|---|---|---|
| Aminoacid source[a] | — | 10.0 | 5.0 |
| Sucrose | 40.0 | 40.0 | 40.0 |
| Glass powder | — | 49.5 | — |
| Dimetilan[a] | 0.5 | 0.5 | 0.5 |
| cis-Nonadecene-9 | 0.03 | — | 0.015 |
| cis-Heneicosene-9 | 0.4 | — | 0.2 |
| cis-Tricosene-9 | 0.3 | — | 0.15 |

The overall results of the groups of tests are summarised in the following table:

TABLE XVI

| Time elapsed in minutes | I-1 | I-2 | I-3 Expected result | I-3 Observed result | Relative synergism |
|---|---|---|---|---|---|
| Total number of dead flies  15 | 5.6 | 20.2 | 12.9 | 35.1 | 2.72 |
| 30 | 6.7 | 24.0 | 15.35 | 40.4 | 2.63 |
| 60 | 8.8 | 28.6 | 18.7 | 44.8 | 2.40 |
| Number of dead flies inside each device at the end of the test | 6.5 | 22.8 | 14.15 | 42.7 | 3.02 |

The results of the preceding experiments show that there is a clearly confirmed synergism between the aminoacid sources and the alkenes defined in the invention.

EXPERIMENT J

The following baits J-1, J-2 and J-3 were prepared as fine powders by intimately mixing the constituents (values in percent by weight):

TABLE XVII

| Composition | J-1 | J-2 | J-3 |
|---|---|---|---|
| Cattle meal | 39.20 | 40.80 | 41.12 |
| Sucrose | 46.00 | 46.00 | 46.00 |
| Hydrolysis product of vegetable proteins | 6.00 | 6.00 | 6.00 |
| Azamethiphos | 0.50 | 0.50 | 0.50 |
| cis-Tricosene-9 | 2.00 | 0.40 | 0.08 |
| Organol Red BS | 0.80 | 0.80 | 0.80 |
| Calcium silicate | 5.00 | 5.00 | 5.00 |
| Calcium sorbate | 0.50 | 0.50 | 0.50 |

These baits were each glued, by means of a glue based on polyvinyl acetate, over the entire inner surface of the lower end of a cylindrical polystyrene box having a radius of 12.5 cm and a height of 7 cm. Three openings of 10 cm² each were cut out of the upper part of the cylinder.

The devices thus prepared were placed, two metres from one another, in a room of 40 m³ kept at a temperature of 25°/26° C. and a relative humidity of about 50.

200 flies of the species Musca domestica were released into the room, and the number of dead flies in the immediate vicinity of each device and in each of the latter was noted every fifteen minutes.

The operation was repeated 12 times, changing the position of the devices each time.

The overall results of the group of tests are summarised in the table below (average number of dead flies per test):

TABLE XVIII

| Time elapsed in minutes | J-1 | J-2 | J-3 |
|---|---|---|---|
| Total number of dead flies  15 | 33.2 | 31.4 | 29.1 |
| 30 | 39.3 | 37.9 | 37.7 |
| 45 | 43.0 | 40.8 | 40.6 |
| 60 | 45.7 | 42.4 | 43.0 |
| 90 | 48.6 | 44.5 | 45.5 |
| 120 | 50.8 | 46.3 | 46.9 |
| Number of dead flies inside each device at the end of the test | 38.3 | 34.2 | 33.7 |

The results of these experiments show that the effectivenesses recorded, when using lure proportions as diverse as 2%, 0.4% and 0.08%, differ very little.

What is claimed is:

1. A bait composition for anthropophilic flies, containing a lure and a food, wherein the lure is present in the composition in a proportion of about 0.05 to 2 percent relative to the weight of the composition and is selected from the group consisting of the cis- stereoisomers of straight-chain alkenes having 19 to 23 carbon atoms in which the ethylenic bond is located after a carbon atom in the 9-position and mixtures of these alkenes, and wherein the food is or contains an aminoacid source of the biochemical class of protides.

2. A composition according to claim 1, wherein the lure is selected from the group consisting of cis-nonadecene-9, cis-docosene-9, cis-heneicosene-9, cis-tricosene-9 and mixtures of two or more of these compounds.

3. A composition according to either of claim 1 or 2, wherein the lure is cis-tricosene-9.

4. A composition according to claim 1, wherein the aminoacid source is present in the food in proportions between 2 and 100% by weight, calculated relative to the weight of the food.

5. A composition according to claim 4, wherein the aminoacid source is present in proportions equal to or greater than 10% by weight, calculated relative to the weight of the food.

6. A composition according to claim 1, wherein the aminoacid source is selected from the group consisting of the products of complete hydrolysis and products of partial hydrolysis of animal and vegetable proteins in the crude state.

7. A composition according to claim 1, wherein the aminoacid source is composed of a mixture of a meat meal and products of complete or partial hydrolysis of proteins.

8. A composition according to claim 1, which contains an insecticidal agent selected from the group consisting of the aromatic and hetero-aromatic esters of N-substituted carbamic acids and the organophosphorus compounds.

9. A composition according to claim 8, wherein the insecticidal agent is present in proportions of about 0.01 to 8% by weight, calculated relative to the total weight of the composition.

10. A composition according to claim 8, wherein the carbamic acid ester is selected from the group consisting of Dimetilan, Dioxacarb, 2-methyl-quinol-8-yl N-methyl-carbamate and mixtures thereof.

11. A composition according to claim 8, wherein the organo-phosphorus insecticide is selected from the group consisting malathion, azamethiphos, fenitrothion and binary and ternary mixtures thereof.

12. A composition according to claim 1, which is in the granulated state with a mean particle size between 0.05 mm and 1 mm.

13. A composition according to claim 1, which comprises about 45 to 72.5 percent of meat meal, about 2.5 to 15 percent of a hydrolysis product of proteins, about 0.1 to 6 percent of an insecticide and about 0.1 to 1 percent of a lure, the remainder of the composition consisting of a carbohydrate and these percentages being by weight, relative to the total weight of the composition.

* * * * *